United States Patent [19]

Coronelli et al.

[11] 3,949,078

[45] Apr. 6, 1976

[54] ANTIBIOTIC ACTIVITIES FROM STREPTOSPORANGIUM VULGARE ATCC 21906

[75] Inventors: Carolina Coronelli; Maria Rosa Bardone; Hermes Pagani, all of Milan, Italy

[73] Assignee: Gruppo Lepetit S.p.A., Milan, Italy

[22] Filed: Jan. 31, 1975

[21] Appl. No.: 546,056

Related U.S. Application Data

[62] Division of Ser. No. 473,023, May 24, 1974, Pat. No. 3,899,396.

[30] Foreign Application Priority Data

May 25, 1973  United Kingdom............... 25160/73

[52] U.S. Cl. .............................................. 424/118

[51] Int. Cl.$^2$.......................................... A61K 35/00
[58] Field of Search..................................... 424/118

[56] References Cited
UNITED STATES PATENTS

| | | | |
|---|---|---|---|
| 3,856,938 | 12/1974 | Murao et al. ........................ | 424/118 |
| 3,862,315 | 1/1975 | Parker et al. ........................ | 424/118 |

*Primary Examiner*—Jerome D. Goldberg
*Attorney, Agent, or Firm*—Theodore Post; C. Kenneth Bjork

[57] ABSTRACT

Antibiotic activities produced by a variety of *Streptosporangium vulgare* named *Streptosporangium vulgare var. antibioticum var. nov.* ATCC 21906. The antibiotic complex contains at least the active fractions named A, B and C.

2 Claims, No Drawings

ANTIBIOTIC ACTIVITIES FROM STREPTOSPORANGIUM VULGARE ATCC 21906

CROSS-REFERENCE TO RELATED APPLICATIONS

This is a division of application Ser. No. 473,023, filed May 24, 1974, now U.S. Pat. No. 3,899,396

SUMMARY OF THE INVENTION

This invention relates to compositions of matter which have antibiotic properties and to methods for the manufacture and use thereof. The antibiotic activities of the invention are produced by a strain of Streptosporangium isolated from a soil sample collected in Bryanston (South Africa) and grown in submerged culture. On the basis of its morphological and physiological properties the new strain was considered a variety of Streptosporangium vulgare and was named Streptosporangium vulgare var. antibioticum var. nov. A sample of this strain was deposited with the A.T.C.C. where it was assigned the number 21906. The antibiotic complex produced by Streptosporangium vulgare ATCC 21906 consists in at least three active fractions named A, B and C, which possess good in vitro and in vivo activity against Gram positive bacteria. Fraction C is endowed also with some antifungal activity.

DESCRIPTION OF THE PREFERRED EMBODIMENTS

Characteristics of the producing strain

To investigate the growth characteristics of strain Streptosporangium vulgare ATCC 21906 the culture was grown on various standard media suggested by Shirling and Gottlieb (Methods for characterization of Streptomyces species, Intern. J. Syst.Bact. 16: 313–338, 1966 and on some media recommended by Waksman (The Actinomycetes, vol. II, The Williams and Wilkins Co., 1961). The morphological and cultural characteristics of Streptosporangium vulgare ATCC 21906 in comparison with those of Streptosporangium vulgare CBS 43361 are reported in Table I. The optimum temperature for development was found to be from 28°C to 37°C and no growth was observed at 50°C. The culture grows abundantly on oatmeal agar, Bennett's and Hickey-Tresner's agar. On some culture media, the vegetative mycelium has coralrose to orange color and the colonies are covered with an abundant rose colored aerial mycelium.

The tests for utilization of carbon compounds were performed according to Pridham and Gottlieb (The utilization of carbon compounds by some Actinomycetales as an aid for species determination. J. Bact. 56: 107 1948.) and the results are shown in Table II. The physiological characteristics of the strain are described in Table III.

Cell wall composition of the new microorganism is shown in Table IV.

TABLE I

Cultural characteristics of Streptosporangium vulgare var. antibioticum var. nov. ATCC 21906 in comparison with Streptosporangium vulgare CBS/433.61.
(SM=substrate mycelium; AM=aerial mycelium)

| MEDIUM | Streptosporangium vulgare var. antibioticum var.nov. ATCC 21906 | Streptosporangium vulgare CBS/433.61 |
|---|---|---|
| Medium No. 2(Yeast extract-malt agar) | SM: abundant, wrinkled, orange to pink, light yellow pigment<br>AM: abundant, powdery, pale pink | SM: abundant, wrinkled, amber to vinaceous<br>AM: abundant, powdery whitish |
| Medium No. 3(Oatmeal agar) | SM: moderate, yellowish<br>AM: good, whitish | SM: moderate, yellowish<br>AM: good, whitish |
| Medium No. 4(Inorganic salts-starch agar) | SM: poor, smooth and thin light yellow<br>AM: none | SM: poor, smooth and thin, yellow<br>AM: none |
| Medium No. 5(Glycerol-asparagine agar) | SM: poor, smooth surface, hyaline<br>AM: none | SM: poor, smooth surface,<br>AM: none |
| Medium No. 6(Peptone-yeast extract iron agar) | SM: poor, slightly wrinkled, amber color<br>AM: none | SM: poor, slightly wrinkled amber color<br>AM: none |
| Medium No. 7(Tyrosine agar) | SM: poor, slightly wrinkled, light brown<br>AM: none | SM: poor, slightly wrinkled light brown<br>AM: none |
| Oatmeal agar | SM: good, wrinkled, pink-coral<br>AM: abundant, powdery, pink-whitish | SM: good, wrinkled, pale coral<br>AM: good, powdery, whitish |
| Hickey and Tresner's agar | SM: abundant, wrinkled, light brown-reddish<br>AM: good, whitish | SM: abundant, wrinkled, dark brown-reddish<br>AM: good, whitish |
| Bennett's agar | SM: abundant, wrinkled, cream color to pink<br>AM: abundant, pink-whitish | SM: abundant, wrinkled, light amber-brown<br>AM: good, whitish |
| Czapek glucose agar | SM: poor, smooth and thin, hyaline<br>AM: none | SM: poor, smooth and thin, amber colored<br>AM: none |
| Glucose asparagine agar | SM: poor, smooth, yellowish<br>AM: none | SM: poor, smooth, yellowish<br>AM: none |
| Nutrient agar | SM: good, wrinkled surface, cream colored<br>AM: none | SM: good, wrinkled surface, amber to vinaceous<br>AM: poor, pinkish |
| Potato agar | SM: good, amber pinkish<br>AM: good, whitish | SM: good, amber colored<br>AM: poor, whitish |
| Calcium malate agar | SM: poor, smooth and flat, light yellow<br>AM: none | SM: poor, smooth and flat hyaline<br>AM: none |
| Skim milk agar | SM: good, wrinkled surface, deep orange<br>AM: none | SM: good, wrinkled surface, deep orange<br>AM: none |
| Egg agar | SM: very scant, hyaline<br>AM: none | SM: very scant, hyaline<br>AM: none |

TABLE I-continued

Cultural characteristics of *Streptosporangium vulgare var. antibioticum*
var. nov. ATCC 21906 in comparison with *Streptosporangium vulgare* CBS/433.61.
(SM=substrate mycelium; AM=aerial mycelium)

| MEDIUM | *Streptosporangium vulgare var. antibioticum var.nov.* ATCC 21906 | *Streptosporangium vulgare* CBS/433.61 |
|---|---|---|
| Peptone glucose agar | SM: poor, wrinkled, cream<br>AM: none | SM: poor, wrinkled, cream<br>AM: none |
| Agar | SM: very scant, hyaline<br>AM: none | SM: very scant, hyaline<br>AM: traces, whitish |
| Loeffler serum | SM: good, orange<br>AM: none | SM: poor, hyaline to cream<br>AM: none |
| Potato | SM: scant, orange<br>AM: none | SM: scant, cream<br>AM: none |
| Gelatin | SM: scant, cream<br>AM: none | SM: scant, cream<br>AM: none |
| Cellulose agar | SM: very scant, hyaline<br>AM: none | SM: very scant, hyaline<br>AM: none |
| Czapek agar | SM: scant, thin hyaline<br>AM: traces, whitish | SM: scant, thin hyaline<br>AM: poor, whitish |

CBS = Centraalbureau Voor Schimmelcultures-Baarn (Netherlands)
The number of the culture media refers to those given by Shirling and Gottlieb.

TABLE II

Utilization of carbon sources by strain ATCC 21906

| Carbon Source | Response |
|---|---|
| Inositol | − |
| Fructose | + |
| Rhamnose | − |
| Mannitol | + |
| Xylose | + |
| Raffinose | − |
| Arabinose | + |
| Cellulose | − |
| Sucrose | + |
| Glucose | + |
| Mannose | − |
| Lactose | + |
| Salicin | − |

TABLE III

Physiological properties of strain ATCC 21906

| TESTS | RESULTS |
|---|---|
| Solubilization of calcium malate | Negative |
| Nitrate reduction | Positive |
| Hydrolysis of starch | Positive |
| $H_2S$ formation | Negative |
| Liquefaction of gelatine | Negative |
| Casein hydrolysis | Positive |
| Litmus milk { coagulation | Positive |
|            { peptonization | Negative |
| Tyrosinase production | Negative |
| Cellulose decomposition | Negative |
| Chromogenic action | Negative |

TABLE IV

Cell-wall composition of strain ATCC/21906

| Isomers of diamino-pimelic acid (DPA) | | Amino Acids | | | Sugars | | |
|---|---|---|---|---|---|---|---|
| LL-DAP | Meso or DD-DAP | Aspartic acid | Glycine | Lysine | Arabinose | Xylose | Galactose |
| TR | ++ | + | + | + | − | TR | ++ |

++ = major component
+ = minor component
TR = trace or doubtful component

Analysis of cell-wall composition was performed according to the method described by B. Becker and H. A. Lechevalier: Chemical composition of cell-wall preparations from strains of various form-genera of aerobic actinomycetes. Appl. Microbiol. 13:236–243, 1965.

At the microscopic examination the aerial mycelium of strain ATCC 21906 revealed to be formed of short highly branched hyphae, on the tip of which a spherical sporangium develops. The average diameter of the aerial mycelium is about 1.0μ. The sporangia are quite variable in size, generally from 7 to 12 μ in diameter. The sporangiospores are disposed in a regular coiled fashion in the interior of the sporangium. The sporangiospores are generally spherical, non-motile, with an average diameter of 1.3 to 1.5μ. The non-motile sporangiospores are characteristic of the genus Streptosporangium according to the key for genera of the family Actinoplanaceae and the cell-wall composition is in accordance.

A comparison of the cultural characteristics of our strain with those reported for the streptosporangia strains so far described showed a similarity with *Streptosporangium vulgare* (Nonomura and Ohara, Distribution of the Actinomycetes in soil. — The isolation and classification of the genus Streptosporangium. J. Ferment. Technol. 38: 405, 1960), however the two strains can be differentiated for the color of the substrate and aerial mycelium on some media as shown by the data reported in Table I.

Since for *Streptosporangium vulgare* there is not described production of antibiotic activity the strain was assigned the name *Streptosporangium vulgare var. antibioticum var. nov.*

Production And Isolation Of the Antibiotic

For the production of the antibiotic activity the strain ATCC 21906 is fermented under submerged conditions in a liquid nutrient medium at 28°C in aerated jars with stirring until substantial antibiotic activity is present. The composition of the nutrient medium may be for instance the following:

| | |
|---|---|
| yeast extract | 1.0 g. |
| soybean meal | 10.0 g. |
| peptone | 4.0 g. |
| meat extract | 4.0 g. |
| dextrose | 50.0 g. |
| $CaCO_3$ | 5.0 g. |
| NaCl | 2.5 g. |
| tap water q.s. to | 1 liter |

The maximum antibiotic activity is obtained after 120–144 hours of fermentation. The microbiological assay is performed by the agar diffusion method using Staphylococcus aureus as the test organism.

For the extraction of the antibiotic activity the culture broth is filtered using Hyflo super-cell as a filter aid, the solution is treated with ethyl acetate, after addition of 1% sodium ascorbate. The solvent is washed with a phosphate buffer solution (pH 7.0) and concentrated in vacuo to a small volume. The resulting concentrate solution is poured into a large volume of light petroleum and a crude powder is obtained having an activity of 0.5 γ/ml against Staphylococcus aureus.

Biological and Chemico-Physical Properties of the Crude Antibiotic

The crude mixture is active in vitro against gram-positive bacteria at concentration values less than 1γ/ml and against gramnegative bacteria at concentration of about 50γ/ml. The crude complex is active at concentrations between 4 and 5γ/ml also against Staphylococcus aureus strains resistant to erythromycin and lincomycin.

Protection at low doses has been obtained against experimental infections in mice by subcutaneous route and at higher doses by oral route.

The antimicrobial spectrum and the results of experimental infections are reported in Table V and VI. The acute toxicity in mice is about 750 mg/kg.

The solubility of the crude mixture is good in alcohols, esters, chloroform and methylene chloride. The ultraviolet spectrum shows an absorption maximum at 260 mμ for solutions at acidic pH and at 290 mμ for solutions at alkaline pH. The pKa spectrophotometrically determined is about 5.5. The infrared spectrum shows intense peaks at 3200–3100 cm.⁻ and 1100–1200 cm.⁻ characteristic for glycosidic moieties. Acid hydrolysis of the mixtue gave substances with characteristic reactions and infrared spectra in accordance with a glycosidic nature of the antibiotic. A more detailed investigation has been carried out on the purified fractions after separation by column chromatography.

Purification of the Antibiotic and Analysis of the Separated Fractions.

The presence of at least three active components has been revealed in the crude product by thin-layer chromatography using chloroform-methanol 95:5 or 98:2 mixtures as eluting system and microbiologial development on Bacillus substilis as detecting system. (Nicolaus et al., II Farmaco Ed. Prat. 8, 350–370, 1961). A separation of the complex has been achieved by column chromatography on activated silica-infusorial earth 50:50 v/v) using chloroform-methanol mixture as eluting system. Three active fractions, named A, B and C, have been obtained. fraction C being still a mixture of two active components.

According to an effective procedure to carry out the separation, 6 g. of the crude complex are chromatographed on a column of 500 g. silica-infusorial earth 50:50 v/v) by eluting with fractions of 200 ml. Component A is eluted by a mixture $CHCl_3:CH_3OH$ 98:2 evaporation of combined fractions 3 through 7 gives 0.655 g. of the product. Evaporation of the subsequent fractions 8 through 15 affords 810 mg. of a mixture of components A and B.

Component B is eluted by mixture $CHCl_3:CH_3OH$ 95:5 and is recovered from fraction 12 through 23. Evaporation of the combined eluates gives 1.1 g. of the pure component B.

Component C is eluted by a mixture $CHCH_3:CH_3OH$ 90:10. Evaporation of the combined fractions 26 and 27 gives 0.935 g. of the product. As reported in Table IV the antibacterial spectra of fraction A and B are quite similar while fraction C shows some antifungal activity. Paper chromatography showed that only one of the two products contained in fractions C has antifungal properties. The chemico-physical data reported in Table VI shows a close relationship between the three fractions; the infrared spectra have the same general appearance and they all contain chlorine and nitrogen. From the microanalytical data of fractions A and B a minimum molecular formula containing two chlorine atoms and one nitrogen atom, with a molecular weight of about 1500, can be deduced. This is confirmed by the mass spectra of the two fractions, where the peaks at 630, 632 and 634 m/e, the highest ion peaks, have relative intensities in agreement with the presence of two chlorine atoms in this fragment. Also the determinations of the molecular weight through the dew point method support the value calculated from the chlorine content.

All three fractions A, B and C (1 g.), when refluxed for 30 minutes 0.1N hydrochloric acid (100 ml.) gave after column chromatography of the methylene chloride extracts of each hydrolyzed mixture the same crystalline product, with m.p. 145°–8°C, $[\alpha]_D^{20}$ (c=0.9% in pyridine for 24 hours):+ 30.9 →: + 17.6,λ max in methanol at 279 mμ, and microanalytical data in accordance for a molecular formula $C_{15}H_{17}O_7Cl_2$. The aqueous phase from the hydrolysis after neutralization by anion exchange resin and evaporation in vacuo gave a solid residue positive to Fehling, ninhydrin, and red tetrazolium tests.

TABLE V

| In vitro spectrum of activity of the crude complex and fractions A, B and C | | | | |
|---|---|---|---|---|
| ORGANISM | CRUDE COMPLEX | Minimal Inhibitory Concentration (γ/nl) | | |
| | | FRACTION A | FRACTION B | FRACTION C |
| Staphylococcus aureus 209 P ATCC 6538 | 0.5 | 0.5 | 0.5 | 1.0 |
| Staphylococcus aureus ATCC 6538 erythromycin/R | 1 | | | |
| Staphylococcus aureus ATCC 6538 lincomycin/R | 1 | | | |
| Staphylococcus aureus Tour | 1.0 | 0.5 | 0.5 | 2.0 |
| Streptococcus hemolyticus C 203 | 0.05 | 0.05 | 0.01 | 0.1 |
| Diplococcus pneumoniae NC 41 | 0.05 | 0.05 | 0.05 | 0.1 |

TABLE V-continued

In vitro spectrum of activity of the crude complex and fractions A, B and C

| ORGANISM | CRUDE COMPLEX | Minimal Inhibitory Concentration ($\gamma$/nl) | | |
|---|---|---|---|---|
| | | FRACTION A | FRACTION B | FRACTION C |
| *Clostridium perfringens* ISS 30543 | 0.05 | 0.05 | 0.05 | 0.5 |
| *Escherichia coli* SK 12140 | 50 | 50 | 100 | 50 |
| *Proteus vulgaris* X 19H ATCC 881 | >100 | >100 | >100 | >100 |
| *Pseudomonas aeruginosa* ATCC 10145 | >100 | >100 | >100 | >100 |
| *Mycoplasma gallisepticum* H21 C.Z.B. | 20 | 10 | 50 | 10 |
| *Mycobacterium tuberculosis* H37$_{Rv}$ ATCC 9360 | 50 | 50 | >50 | 5 |
| *Candida albicans* SKF 2270 | 20 | >100 | >100 | 10 |
| *Trichophyton mentagrophytes* SKF 17410 | 50 | >100 | >100 | 10 |

TABLE VI

In vivo activity of the crude complex and fractions, A, B and C (mg/kg)

| ORGANISM | TREATMENT ROUTE | CRUDE COMPLEX (ED$_{50}$) | FRACTION A (ED$_{50}$) | FRACTION B | FRACTION C |
|---|---|---|---|---|---|
| *Streptococcus hemolyticus* C 203 | s.c. | 7.5 | 7.5 | 15 (ED$_{100}$) | 50 (ED$_{100}$) |
| *Staphylococcus hemolyticus* C 203 | p.o. | 250 | 120 | 200 (ED$_{80}$) | — |
| *Staphylococcus aureus* Tour | s.c. | 90 | — | — | — |
| *Diplococcus pneumoniae* UC 41 | s.c. | 20 | — | — | — |

TABLE VII

Chemico-physical properties of fractions A, B and C.

| PROPERTIES | FRACTION A | FRACTION B | FRACTION C |
|---|---|---|---|
| Rf* | 0.39 | 0.2 | 0.07 |
| Microanalytical data | C = 51.8 | C = 52.2 | Nitrogen and chlorine present |
| | H = 6.3 | H = 6.4 | No quantitative data reported |
| | N = 0.9 | N = 0.95 | because fraction C is a |
| | Cl = 4.3 | Cl = 4.3 | mixture of two components |
| I.R. spectra** cm$^{-1}$ | 3450(i)-1720(m)-1680(m)- 1570(w)-1150-1000(i) | 3460(i)-1720(m)- 1570(w)-1150-1000(i) | 3460(i)-1720(m)-1650(m)- 1550(m)-1150-1000(i) |
| Mass spectra m/e | 630 highest ion peak 380 233 base peak 250 218 | 630 highest ion peak 380 233 base peak 250 218 | 630 highest ion peak 380 233 base peak 250 218 |

*Support: Silica gel G/HF$_{254}$ plates. Solvent system = chloroform:methanol 98:2 (10 × 2 cm). Antibiotics detected by development with concentrated H$_2$SO$_4$ at 100°C.
**Infrared spectrum in nujol mull; intense peak = i; medium peak = m; weak peak = w.

We claim:

1. An antibiotically effective composition of matter identified as fraction A, said fraction A being an organic substance having the following characteristics:
   a. Elemental analysis: C = 51.8; H = 6.3; N = 0.9; Cl = 4.3
   b. Rf on silica gel plates with a solvent system chloroform: methanol 98:2 = 0.39
   c. Molecular weight of about 1500 d. I.R. absorption bands at the following frequencies: 3450(i); 1720(m); 1680(m); 1570(w); 1150-1000(i)
   c. Mass spectrum showing ion peaks at the following m/c values: 630, 380, 233, 250, 218 said composition of matter being further characterized in that it has glycosidic nature and it gives by acid hydrolysis with 0.1N hydrochloric acid a substance with melting point 145°-8°C, molecular formula C$_{15}$H$_{17}$O$_7$Cl$_2$ and [$\alpha$]$_D^{20}$ (c=0.9% in pyridine for 24 hours):+30.9 → +17.6.

2. A composition of matter identified as fraction B, said fraction B being an organic substance having the following characteristics:
   a. Elemental analysis: C=52.2; H=6.4; N=0.95; Cl=4.3
   b. Rf on silicagel plates with a solvent system chloroform:methanol 98:2 = 0.2
   c. I.R. absorption bands at the following frequencies: 3460(i); 1720(m); 1570(w); 1150-1000(i)
   e. Mass spectrum showing ion peaks at the following m/e values: 630, 380, 233, 250, 218 said composition of matter being further characterized in that it has glycosidic nature and it gives by acid hydrolysis with 0.1N hydrochloric acid a substance with melting point 145°-8°C, molecular formula C$_{15}$H$_{17}$O$_7$Cl$_2$ and [$\alpha$]$_D^{20}$(c=0.9% in pyridine for 24 hours):30.9 → +17.6.

* * * * *

UNITED STATES PATENT AND TRADEMARK OFFICE
CERTIFICATE OF CORRECTION

PATENT NO. : 3,949,078
DATED : April 6, 1976
INVENTOR(S) : Coronelli et al

It is certified that error appears in the above—identified patent and that said Letters Patent are hereby corrected as shown below:

Column 2, line 26, "107 1948" should read --107, 1948--;

Columns 1 and 2, TABLE I, 3rd column, to be corrected as follows:

line 3, should read --AM: abundant, powdery, whitish--;

line 6, should read --SM: poor, smooth and thin, light--;

line 9, should read --SM: poor, smooth surface, hyaline--;

line 11, should read --SM: poor, slightly wrinkled,--;

line 14, should read --SM: poor, slightly wrinkled,--;

line 17, should read --SM: good, wrinkled, pale pink- --;

line 36, should read --SM: poor, smooth and flat,--;

Column 4, line 33, "for genera" should read --for the genera--;

Column 5, line 16, "ascorbate The" should read --ascorbate. The--;

Column 5, line 27, "gramnegative" should read --gram-negative--;

Column 5, line 44, "3200-3100 cm.$^{-}$" should read --3200-3100 cm.$^{-1}$--

Column 5, line 45, "cm.$^{-}$" should read --cm.$^{-1}$--;

Column 5, line 46, "mixtue" should read --mixture--;

UNITED STATES PATENT AND TRADEMARK OFFICE
CERTIFICATE OF CORRECTION

PATENT NO. : 3,949,078
DATED : April 6, 1976
INVENTOR(S) : Coronelli et al

It is certified that error appears in the above-identified patent and that said Letters Patent are hereby corrected as shown below:

Column 6, line 6, "earth50:50 v/v)" should read --earth (50:50 v/v)

Column 6, line 8, "obtained.fraction" should read --obtained, fraction--;

Column 6, line 19, "by mixture" should read --by a mixture--;

Column 6, line 29, "in fractions C" should read --in fraction C--;

Column 6, line 31, "shows" should read --show--;

Columns 5 and 6, TABLE V, line 2 of heading "($\gamma$/nl) should read --($\gamma$/ml)--;

Columns 7 and 8, TABLE V-continued, line 2 of heading "($\gamma$/nl)" should read --($\gamma$/ml)--.

Column 7, line 50, "c. Molecular weight of about 1500 d. I.R. absorption" should read --c. Molecular weight of about 1500--

Column 7, line 51 (additional line or lines), should read --d. I.R. absorption bands at the following frequencies: 3450(i); 1720(m); 1680(m); 1570(w); 1150-1000(i)--.

Signed and Sealed this

Thirteenth Day of July 1976

[SEAL]

Attest:

RUTH C. MASON
Attesting Officer

C. MARSHALL DANN
Commissioner of Patents and Trademarks